United States Patent
Dargam et al.

(10) Patent No.: US 11,771,378 B2
(45) Date of Patent: Oct. 3, 2023

(54) SYSTEMS AND METHODS FOR QUANTIFYING DURATION OF HEART SOUNDS

(71) Applicants: Valentina Dargam, Miami, FL (US); Joshua Daniel Hutcheson, Miami, FL (US)

(72) Inventors: Valentina Dargam, Miami, FL (US); Joshua Daniel Hutcheson, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 18/147,969

(22) Filed: Dec. 29, 2022

(65) Prior Publication Data

US 2023/0210469 A1   Jul. 6, 2023

Related U.S. Application Data

(60) Provisional application No. 63/266,248, filed on Dec. 30, 2021.

(51) Int. Cl.
   *A61B 5/00*   (2006.01)

(52) U.S. Cl.
   CPC ............ *A61B 5/7264* (2013.01); *A61B 5/725* (2013.01); *A61B 5/7246* (2013.01); *A61B 5/7257* (2013.01)

(58) Field of Classification Search
   CPC ......... A61B 5/0205; A61B 7/00; A61B 7/003; A61B 5/021; A61B 5/0215; A61B 5/352; A61B 5/7285; A61B 5/7264; A61B 5/7246; A61B 5/725; A61B 5/7257; A61M 5/1723; A61N 1/36585
   See application file for complete search history.

(56) References Cited

U.S. PATENT DOCUMENTS

| | | | |
|---|---|---|---|
| 8,597,197 B2* | 12/2013 | Patangay | A61B 7/04 600/528 |
| 10,130,267 B2 | 11/2018 | Song et al. | |
| 2013/0131530 A1* | 5/2013 | Brockway | A61B 7/00 600/513 |
| 2020/0297230 A1* | 9/2020 | Thakur | A61B 5/053 |

* cited by examiner

*Primary Examiner* — Rex R Holmes
(74) *Attorney, Agent, or Firm* — Saliwanchik, Lloyd & Eisenschenk

(57) ABSTRACT

Systems and methods for quantifying the duration of S1 and/or S2 heart sounds, in order to identify markers of heart failure and/or lung failure, are provided. Cardiac cycles containing S1 and S2 sound can be identified in a phonocardiogram and normalized. In order to quantify S1 and S2 sound length, the envelope of the absolute value of the signal can be obtained for each cycle. The sound waves of two components can be separated using the identified single sound wave. These features can be correlated to measures of heart failure and/or lung failure.

16 Claims, 11 Drawing Sheets

SYSTEMS AND METHODS FOR QUANTIFYING DURATION OF HEART SOUNDS

CROSS-REFERENCE TO RELATED APPLICATION

This application claims the benefit of U.S. Provisional Application Ser. No. 63/266,248, filed Dec. 30, 2021, the disclosure of which is hereby incorporated by reference in its entirely, including all figures, tables, and drawings.

GOVERNMENT SUPPORT

This invention was made with government support under 1648451 awarded by National Science Foundation. The government has certain rights in the invention.

BACKGROUND

Pulmonary hypertension is a disease in which pressure in vessels (e.g., pulmonary artery) that lead from the heart to the lungs is abnormally high. When this pressure is too high, it can be classified as pulmonary hypertension. This disease can be caused by different underlying conditions, but for all underlaying causes, if the pressure is too high it can lead to right-sided heart failure.

Heart failure is a leading cause of cardiovascular morbidity. Regular monitoring of heart failure patients is critical to assess therapeutic efficacy and prevent or inhibit unneeded hospitalizations, especially in underserved populations that are disproportionately affected by cardiovascular disease. Implantable devices (e.g., CardioMEMS) have emerged recently as technology to monitor cardiac function in heart failure patients. These devices wirelessly transmit pulmonary artery pressure, a surrogate marker of cardiac function, to an external antenna. While these devices can be effective in aiding physicians in heart failure monitoring, they have not been widely adopted due to the high costs associated with the implantation procedure.

BRIEF SUMMARY

Embodiments of the subject invention provide novel and advantageous systems and methods for quantifying the duration of S1 and/or S2 heart sounds in order to identify markers of heart failure and/or lung failure. Split time between the components (e.g., T1 and P2) can also be quantified. Cardiac cycles containing S1 and S2 sound can be identified in a phonocardiogram and normalized. In order to quantify S1 and S2 sound length, the envelope of the absolute value of the signal can be obtained for each cycle. The sound waves of two components (e.g., M1 and T1) can be separated using the identified single sound wave (e.g., S1 sound). These features can be correlated to measures of heart failure and/or lung failure, including but not limited to pulmonary pressure, right ventricular systolic pressure, right ventricular diastolic pressure, and ejection fraction.

In an embodiment, a system for identifying at least one marker of heart failure by quantifying a duration of an S1 heart sound and a duration of an S2 heart sound can comprise: a processor; and a (non-transitory) machine-readable medium (e.g., a (non-transitory) computer-readable medium) in operable communication with the processor and having instructions stored thereon that, when executed by the processor, perform the following steps: receiving a signal including information of activity of a heart of a first patient; identifying at least one cardiac cycle including the S1 heart sound and the S2 heart sound; normalizing the at least one cardiac cycle; calculating a short-time Fourier transform of the signal; calculating an envelope of the signal using the short-time Fourier transform and the normalized at least one cardiac cycle; determining features of the signal based on the envelope of the signal, the features of the signal comprising the duration of the S1 heart sound and the duration of the S2 heart sound; and correlating the features of the signal to measures of heart failure to identify the at least one marker of heart failure, the at least one marker of heart failure comprising any measure of heart failure with a strong correlation to the features of the signal. The signal can be, for example, a phonocardiogram signal. The system can further include a phonocardiograph used for recording the phonocardiogram. The phonocardiograph can be in operable communication with (e.g., communicating wirelessly or via a wire) with the processor, or the phonocardiograph can be not in operable communication with the processor, and the phonocardiogram can be provided to the machine-readable medium and/or the processor via other means (e.g., via an intermediary such as removable memory). The system can further comprise a display in operable communication with the processor and the machine-readable medium, and the instructions when executed can further cause the at least one marker heart failure on the display. The features of the signal can further comprise a split time of the S1 heart sound, a split time of the S2 heart sound, a loudness of the S1 heart sound, and/or a loudness of the S2 heart sound. The measures of heart failure can comprise, for example, pulmonary pressure, right ventricular pressure, and/or ejection fraction. The determining of the features of the signal based on the envelope of the signal can comprise: obtaining an envelope curve using a Hilbert transform on the envelope signal; and/or obtaining a start and an end of the envelope signal for each cycle. The instructions when executed can further perform the step of using the at least one marker of heart failure to non-invasively monitor for heart failure of a patient (e.g., the first patient or a second patient) by checking the duration of the S2 sound of the patient. The correlating of the features of the signal to the measures of heart failure can comprise using an algorithm. The calculating of the envelope of the signal can comprise using a filtering technique and/or an averaging technique.

In another embodiment, a method for identifying at least one marker of heart failure by quantifying a duration of an S1 heart sound and a duration of an S2 heart sound can comprise: receiving (e.g., by a processor, which may be in operable communication with a (non-transitory) machine-readable medium having instructions stored thereon as disclosed above) a signal including information of activity of a heart of a first patient; identifying (e.g., by the processor) at least one cardiac cycle including the S1 heart sound and the S2 heart sound; normalizing (e.g., by the processor) the at least one cardiac cycle; calculating (e.g., by the processor) a short-time Fourier transform of the signal; calculating (e.g., by the processor) an envelope of the signal using the short-time Fourier transform and the normalized at least one cardiac cycle; determining (e.g., by the processor) features of the signal based on the envelope of the signal, the features of the signal comprising the duration of the S1 heart sound and the duration of the S2 heart sound; and correlating (e.g., by the processor) the features of the signal to measures of heart failure to identify the at least one marker of heart failure, the at least one marker of heart failure comprising any measure of heart failure with a strong correlation to the features of the signal. The signal can be, for example, a phonocardiogram signal. The method can further comprise recording the phonocardiogram by a phonocardiograph as disclosed above. The method can further comprise displaying the at least one marker of heart failure on a display (e.g., a display in operable communication with the processor). The features of the signal can further comprise a split time of the S1 heart sound, a split time of the S2 heart sound, a loudness of the S1 heart sound, and/or a loudness of the S2 heart sound. The measures of heart failure can comprise, for example, pulmonary pressure, right ventricular pressure, and/or ejection fraction. The determining of the features of the signal based on the envelope of the signal can comprise: obtaining an envelope curve using a Hilbert transform on the envelope signal; and/or obtaining a start and an end of the envelope signal for each cycle. The method can further comprise using the at least one marker of heart failure to non-invasively monitor for heart failure of a patient (e.g., the first patient or a second patient) by checking the duration of the S2 sound of the patient. The correlating of the features of the signal to the measures of heart failure can comprise using an algorithm. The calculating of the envelope of the signal can comprise using a filtering technique and/or an averaging technique.

BRIEF DESCRIPTION OF DRAWINGS

FIG. 1A shows a plot of left ventricular (LV) mass per body weight (BW) (in milligrams per gram (mg/g)), and p is less than 0.01. FIG. 1B shows a plot of LV posterior wall thickness at diastole (PWd) per BW (in millimeters per gram (mm/g)), and p=0.00089. FIG. 1C shows a plot of reduced ventricular end diastolic volume (in microliters (µL)), and p=0.013. FIG. 1D shows a plot of increased injection fraction (in percentage (%)), and p=0.0002.

FIG. 2A shows a plot of mean pulmonary artery pressure (mPAP) (in millimeters of mercury (mmHg), and p is less than 0.001. FIG. 2B shows a plot of the ratio of pulmonary acceleration time per pulmonary ejection time (PAT/PET), and p=0.0012. FIG. 2C shows a plot of S2 sound duration at week 12 (W12) (in milliseconds (ms)), and p=0.000002.

In FIG. 6A, the p values at 3 weeks, 6 weeks, 9 weeks, and 12 weeks were not significant (NS), NS, NS, and 0.092, respectively. In FIG. 6B, the p values at 3 weeks, 6 weeks, 9 weeks, and 12 weeks were 0.024, 0.073, 0.008, and NS, respectively. In FIG. 6C, the p values at 3 weeks, 6 weeks, 9 weeks, and 12 weeks were NS, NS, 0.054, and 0.011, respectively. Adenine groups showed markers of heart failure with preserved ejection fraction. Prolonged deceleration time (in FIG. 6C) due to prolonged relation implies grade I diastolic dysfunction.

FIG. 11 shows a positive correlation between S2 duration and RV pressure.

DETAILED DESCRIPTION

Figures 1A, 1B, 1C, 1D:
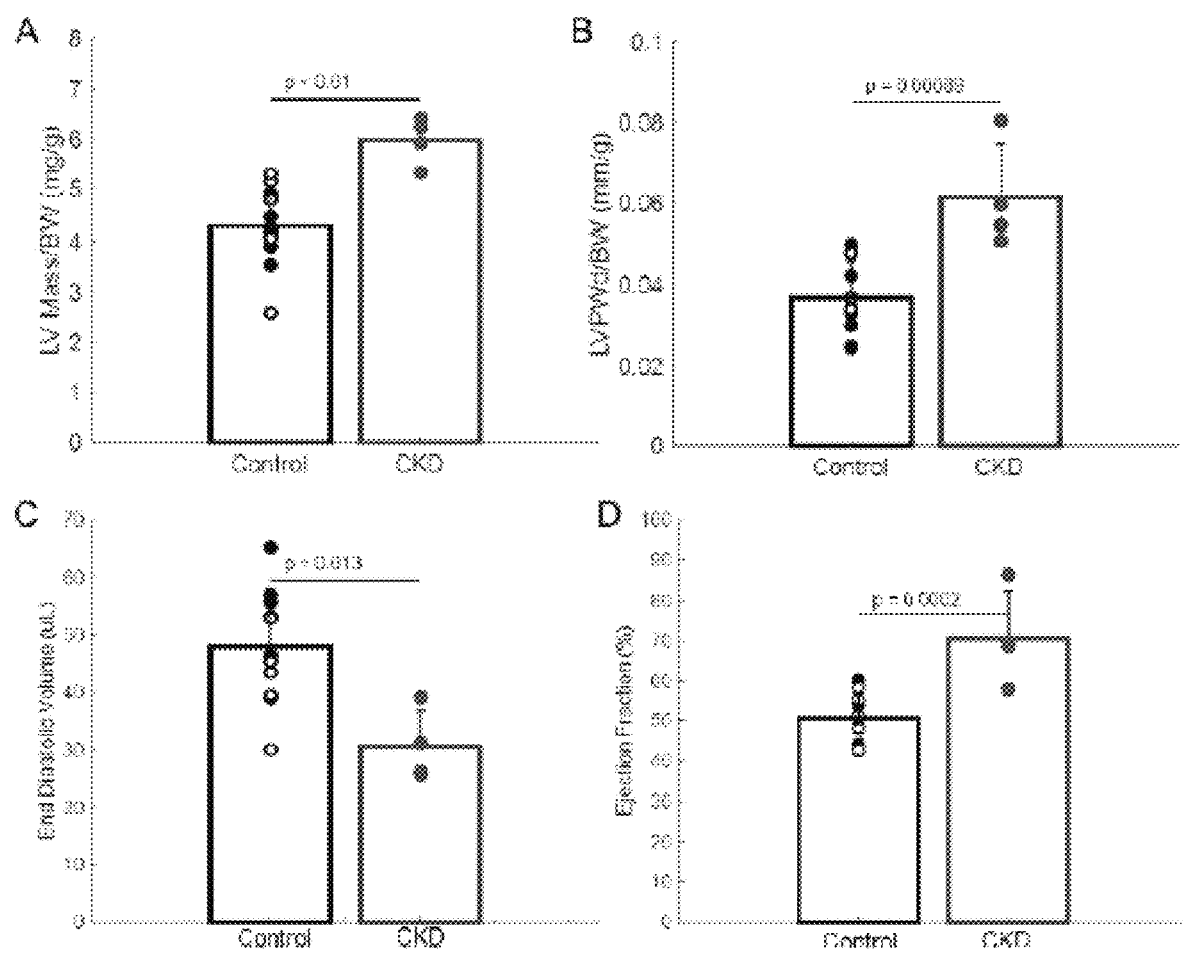
FIGS. 1A-1D show bar charts for echocardiographic measures for heart failure with preserved ejection fraction (HFpEF), each showing a control versus a chronic kidney disease (CKD)-induced model of HFpEF. In each plot, the control is the left bar, and the CKD-induced model is the right bar.

Embodiments of the subject invention provide novel and advantageous systems and methods for quantifying the duration of S1 and/or S2 heart sounds in order to identify markers of heart failure and/or lung failure. Split time between the components (e.g., T1 and P2) can also be quantified. Cardiac cycles containing S1 and S2 sound can be identified in a phonocardiogram and normalized. In order to quantify S1 and S2 sound length, the envelope of the absolute value of the signal can be obtained for each cycle. The sound waves of two components (e.g., M1 and T1) can be separated using the identified single sound wave (e.g., S1 sound). These features can be correlated to measures of heart failure and/or lung failure, including but not limited to pulmonary pressure, right ventricular systolic pressure, right ventricular diastolic pressure, and ejection fraction.

In pulmonary hypertension, the increased right-sided cardiac load causes a delay in ventricular and atrium chamber emptying. Chamber emptying includes ejection of blood to another cardiac structure or systemic circulation. The chamber ends its emptying period once differential pressure between the emptying chamber (e.g., right ventricle) and other cardiac structure (e.g., pulmonary artery) reaches approximately 0 millimeters of mercury (mmHg). When this occurs, either the pulmonary valve or the tricuspid valve closes to allow chamber filling. In pathophysiological conditions of pulmonary hypertension, there is a delay in pulmonary and tricuspid valve closure due to increased pressure(s), either right-sided heart pressure(s) or pulmonary artery pressure(s). The increased pressure(s) also lead to a louder sound of pulmonary and tricuspid valve closure. The S1 heart sound for the closure of the tricuspid (T1) and mitral (M1) valves, while the S2 sound is for the closure of the aortic (A2) and pulmonary (P2) valves. Under physiological conditions, closure of the mitral and aortic valves precede closure of the tricuspid and pulmonary valve. The delay in tricuspid and pulmonary valve closure due to increased right-sided heart pressures leads to a delay in time of closure that can be identified using heart sounds. Additionally, valve closure amplitude can also be identified for each component using heart sounds.

Changes in cardiothoracic pressures influence heart sounds. Heart sound duration correlates to increased right ventricular (RV) pressure. Most commonly, an increase in RV pressure is caused by increases in left ventricular (LV) and pulmonary artery pressures. Pulmonary hypertension is a disease characterized by increased pressure in vessels (e.g., pulmonary artery) that lead from the heart to the lungs. When this pressure is too high, it can lead to heart failure. Similarly, increases in left and right ventricular pressures increase cardiac load that can eventually lead to heart failure. Changes in cardiothoracic pressures can be caused by different and multiple underlying conditions. Regardless of the underlying cause, changes in cardiothoracic structure can be indicative of disease. An increase in RV pressure is a marker of advanced disease progression of both pulmonary hypertension and LV failure. In fact, markers of RV function are independent predictors of death and adverse outcomes in patients with various cardiac conditions. The increased right-sided cardiac load causes a delay in ventricular and atrium chamber emptying. Chamber emptying is characterized by ejection of blood to another cardiac structure or systemic circulation. The chamber ends its emptying period once differential pressure between the emptying chamber (e.g., right ventricle) and other cardiac structure (e.g., pulmonary artery) reaches approximately 0 mmHg. When this occurs, either the pulmonary or tricuspid valve close to allow chamber filling.

Cardiac valves closure is caused by differences in pressures between the corresponding cardiac structures. Closure of cardiac valves produce the sounds heard through a physician's stethoscopes. Under physiological conditions, valve closures produce the S1 and S2 sounds. The S1 heart sound is due to the closure of the tricuspid (T1) and mitral (M1) valves, while the S2 sound is due to the closure of the aortic (A2) and pulmonary (P2) valves. The time between valve closure for each sound is known as the split time. Changes in cardiothoracic pressures and filling volumes lead to differences in split time of the S1 and S2 sounds. Physiologically, there are differences in the split time of the S2 sound due to changes in cardiothoracic pressure influenced by respiration. In pathophysiological conditions, the split time of the S2 sound can be altered. An increase in RV pressure leads to a fixed split time and there is a delay in pulmonary valve (P2) closure due to right-ventricular failure. In pulmonary hypertension without RV failure, there is a narrow split time due to increased pulmonary artery pressures. These changes in split time also occur due to changes in cardiac filling volume. This change in either tricuspid or pulmonary valve closure due to different pathological conditions can be identified using heart sounds. Additionally, valve closure loudness can also be used to differentiate between healthy and diseased sounds because the increased cardiothoracic pressures lead to a louder sound of pulmonary and/or tricuspid valve closure.

Embodiments of the subject invention can quantify features of S1 and/or S2 sounds that correlate to markers of heart disease and/or lung disease. These markers can include timing of valve closures, split times, and/or sound duration. First, cardiac cycles containing S1 and S2 sound can be identified in a signal (e.g., a phonocardiogram signal) and normalized. The short-time Fourier transform of the signal (e.g., phonocardiogram signal) can be identified. Both the time domain signal (e.g., phonocardiogram signal) and the short-time Fourier transform signal can be used to identify the envelope. In order to find the components of each sound, the envelope curve of the signal can be obtained using the Hilbert transform. Different types of signal envelopes can be computed using different filtering and averaging techniques. Features of the upper and lower envelopes can be used to determine the location of each sound component (e.g. A2 and P2). The location of each component can be used to determine the split time. These features of the upper and lower envelopes can include envelope peaks, root mean square, and/or amplitude. In order to quantify S1 and S2 sound length, the threshold for the start and ending of the envelope signal can be obtained for each cycle. Sound duration can be identified for all cycles, with or without reference to respiratory phase, by identifying the duration of the envelope. The area under the envelope can also be quantified as a feature of sound loudness. Split time can be quantified by: 1) identifying the starts of sound components (e.g. M1 and T1) in reference to a signal and its envelope; and 2) decomposition of the components using nonstationary signal decomposition. These features can be correlated to measures of right-sided heart failure, including but not limited to pulmonary pressure, right ventricular systolic and diastolic pressure, and/or ejection fraction. Measures of disease can be classified using echocardiography and cardiac catheterization. Features that correlate well with pathophysiological findings can be identified (e.g., by an algorithm), and the confidence interval of the associated pathophysiology to the feature identified can be displayed (e.g., on a display in operable communication with a processor that executes instructions to identify the feature(s)). S2 duration correlates to mean pulmonary arterial pressure (mPAP) and also to RV pressure (see, e.g., Example 2).

Embodiments of the subject invention are based on the discovery that heart sound duration is correlated to pulmonary hypertension. Systems and methods of embodiments of the subject invention can quantify the duration of S1 and/or S2 sounds, optionally as well as split time between the components (e.g., T1 and P2), to identify markers of right-sided heart failure. First, cardiac cycles containing S1 and S2 sounds can be identified in a phonocardiogram and normalized. In order to quantify S1 and S2 sound length, the envelope of the absolute value of the signal can be obtained for each cycle. Sound duration can be identified for all cycles, with or without reference to respiratory phase, by identifying the length of the envelope. The area under the envelope can also be quantified as a feature of sound loudness.

Split time can be quantified by: 1) identifying the starts of sound components (e.g., M1 and T1) in reference to signal and its envelope; and 2) decomposition of the components using nonstationary signal decomposition. These features can be correlated to measures of right-sided heart failure, including but not limited to pulmonary pressure, right ventricular systolic pressure, right ventricular diastolic pressure, and ejection fraction. Measures of disease can be classified using echocardiography and/or cardiac catheterization. Features that correlate well with pathophysiological findings can be identified (e.g., via an algorithm), and the confidence interval of the associated pathophysiology to the feature identified can be displayed (e.g., on a display). Findings have shown that S2 duration correlates to mean pulmonary arterial pressure (mPAP).

In many embodiments, an algorithm can be used to identify features of heart sounds and their correlation to heart disease and/or lung disease. The algorithm can identify valvular sound components (e.g., M1 and/or T1), timing between components (e.g., split time), duration of sound (e.g., S1 and/or S2 sounds), and/or loudness (e.g., amplitude of components and/or ratios). Then, the altered features identified in the recording can be displayed, as can whether these features correlate to abnormal cardiothoracic function. The features and/or how they correlate to the presence of abnormal cardiac function can be displayed on a display in operable communication with a processor that executes the algorithm and/or a medium (e.g., a memory and/or a (non-transitory) machine-readable medium, such as a computer-readable medium) having the algorithm stored thereon (e.g., in the form of instructions that, when executed by a processor perform the steps of the algorithm).

Embodiments of the subject invention can yield low-cost point-of-care techniques to assess heart function, particularly in underserved populations. Screening techniques to identify heart failure include an extensive medical history, patient reported symptom(s), and a physical examination. However, these are all subjective measure s and can be missed by both patients and medical professionals (e.g., doctors). Currently, the only way to monitor patients with diagnosed heart failure is to implant a wireless device in the pulmonary artery that relays information to the physician so that the physician can intervene when necessary. Such a device is both invasive and expensive, which makes it inaccessible to a large population of patients. In contrast, embodiments of the subject invention (e.g., when paired with existing digital stethoscopes) can reduce the cost and burden of managing patients with heart failure.

In an embodiment, a system can comprise a processor, a display in operable communication with the processor, and a (non-transitory) machine-readable medium (e.g., a computer-readable medium) in operable communication with the processor and having instructions stored thereon that, when executed by the processor perform steps to quantify the duration of S1 and/or S2 sounds, as well as split time between the components (e.g., T1 and P2), in order to identify markers of right-sided heart failure. First, cardiac cycles containing S1 and S2 sound can be identified in a phonocardiogram and normalized. A phonocardiogram is a digital recording of heart sounds that can be obtained using existing devices (e.g., stethoscopes such as digital stethoscopes). In order to quantify S1 and S2 sound length, the envelope of the absolute value of the signal can be obtained for each cycle. Sound duration can be identified for all cycles, with or without reference to respiratory phase, by identifying the length of the envelope. The envelope of a signal is defined as a smooth outline of the highest values of the signal. The area under the envelope can also be quantified as a feature of sound loudness. Split time can be quantified by: 1) identifying the starts of sound components (e.g., M1 and T1) in reference to the raw signal and its envelope; and 2) decomposition of the components using nonstationary signal decomposition. Nonstationary signal decomposition is a method used to separate multiple components of a signal. In embodiments, the sound waves of two components (e.g., M1 and T1) can be separated using the identified single sound wave (e.g., S1 sound). These features can be correlated to measures of right-sided heart failure, including but not limited to pulmonary pressure, right ventricular systolic pressure, right ventricular diastolic pressure, and ejection fraction. Measures of disease can be classified using echocardiography and/or cardiac catheterization. Features that correlate well with pathophysiological findings can be identified (e.g., via an algorithm), and the confidence interval of the associated pathophysiology to the feature identified can be displayed.

Embodiments of the subject invention can utilize digitally recorded heart sounds as a lower cost, non-invasive alternative for monitoring pulmonary pressure (as compared to implantable devices). The second (S2) heart sound derives from closure of the aortic and pulmonary valve at the beginning of diastole. Elevated pulmonary pressure delays the opening and closing of the pulmonary valve, lengthening the duration of the S2 sound. Using a mouse model of chronic kidney disease (CKD), a recognized risk factor for heart failure, preliminary data indicate that S2 sound duration correlates with pulmonary pressure and decreased cardiac function indicative of heart failure.

Embodiments of the subject invention provide non-invasive point-of-care techniques to evaluate changes in cardiac remodeling and function in a model of heart failure with preserved ejection fraction (HFpEF). HFpEF occurs due to stiffening and thickening of the left ventricle wall. The smaller, less compliant chamber cannot fill with a normal volume of blood. Though the fraction of blood ejected with each beat can remain normal, the volume of blood pumped is reduced. Patients with HFpEF require regular monitoring to help physicians evaluate treatment efficacy and prevent unnecessary hospitalizations.

Reduced left ventricular filling results in increased pressure in the left atrium. This also leads to increased pulmonary artery pressure because pulmonic circulation ends at the left atrium. Using the implantable devices, physicians can acquire periodic data related to cardiac function. While such devices have proven efficacious in HFpEF management, the associated high costs and concerns with implantation make them unsuitable for many patients, especially in underserved populations.

The "lub dub" heart sounds heard through a stethoscope result from opening and closing of the cardiac valves as pressures change during the cardiac cycle. The S2 "dub" sound occurs due to closure of the aortic (A2) and pulmonary (P2) valves. Increased pulmonary artery pressure delays right ventricle emptying and pulmonary valve closure. As a result, the P2 component becomes more widely split from the A2 component, resulting in a prolonged S2 sound. Therefore, S2 sound length can serve as a non-invasive measure of pulmonary pressure and cardiac function in HFpEF.

Circulating biomarkers can also provide insight into cardiac remodeling independent of changes in function. Cardiac troponin I (CTnI), released from myocytes in response to myocardial injury, can be used to diagnose acute heart failure and as a prognostic indicator in chronic heart failure. In addition, B-type natriuretic peptide (BNP) and its N-terminal pro-peptide counterpart (NT-proBNP) can be used as sensitive indicators of changes in myocardial stretch in cardiomyopathies. The utility of these biomarkers have led to the adoption of clinical cut-off values used to define normal versus abnormal ranges. However, the evolution of these biomarkers over the course of HFpEF is not well understood. It is hypothesized by the present inventors that increased serum levels of CTnI and NT-proBNP are due to subtle alterations in heart remodeling that precede detectable changes in cardiac function.

Embodiments can correlate S2 sound length to pulmonary artery pressure and cardiac function and remodeling (e.g., Example 1 shows this in a mouse model of HFpEF). Heart sounds can be digitally recorded at early, intermediate, and late stages of HFpEF development and S2 length can be correlated to catheter-based measures of pulmonary pressure and echocardiography assessment of cardiac function.

It is hypothesized that CTnI and NT-proBNP serum markers can be correlated to S2 sound length, pulmonary artery pressure, and cardiac function and remodeling (e.g., in a mouse model of HFpEF). In addition to their utility in acute heart failure assessment, levels of both CTnI and NT-proBNP can help stratify future risk. It is hypothesized that the predictive value of these biomarkers is related to subtly altered cardiac remodeling and mechanics in early stages of heart failure. Circulating concentrations of the biomarkers could be correlated to measurements of cardiac function (e.g., S2 length, pulmonary pressure, echocardiographic assessment) and remodeling (e.g., using histological endpoint assessments at early, intermediate, and late stage HFpEF).

Embodiments of the subject invention can use S2 length as a measure of pulmonary pressure in HFpEF patients and correlate circulating biomarkers to cardiac function and remodeling. Non-invasive heart sound recordings can provide a low-cost, non-invasive alternative to implantable devices (e.g., CardioMEMS). Coupled with biomarker assessment of cardiac remodeling, this can yield a novel point-of-care assessment of HFpEF for underserved patients.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., sub-ranges within the disclosed range), specific embodiments therein are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

Example 1

CKD was induced in eight-week-old C57BL/6J wild-type mice by supplementing chow pellets with 0.2% adenine for 12 weeks. Preliminary analysis of cardiac function was performed in a cohort of mice with CKD (n=4) compared to chow fed control mice (n=11). FIGS. 1A-1D show the results. Referring to FIGS. 1A-1D, data show indications of HFpEF following the 12-week diet in these mice, including elevated left ventricular mass (FIG. 1A) and echocardiographic assessment of left ventricular posterior wall thickness at diastole (FIG. 1B), reduced ventricular end diastolic volume (FIG. 1C), and increased ejection fraction (FIG. 1D).

Kidney dysfunction was apparent after 6 weeks of the diet and became progressively worse up to the 12-week time point. Functional cardiac changes following 3, 6, 9, and 12 weeks of the adenine diet can be assessed using the same echocardiographic measurements demonstrated in FIGS. 1A-1D. Age-matched, chow-fed control mice can be used for baseline comparisons at each time point. Sixteen mice per time point can be used to complete these analyses and the measurements detailed below, including equal numbers of male and female mice to assess potential sex-dependent differences.

Figures 2A, 2B, 2C, 2D:
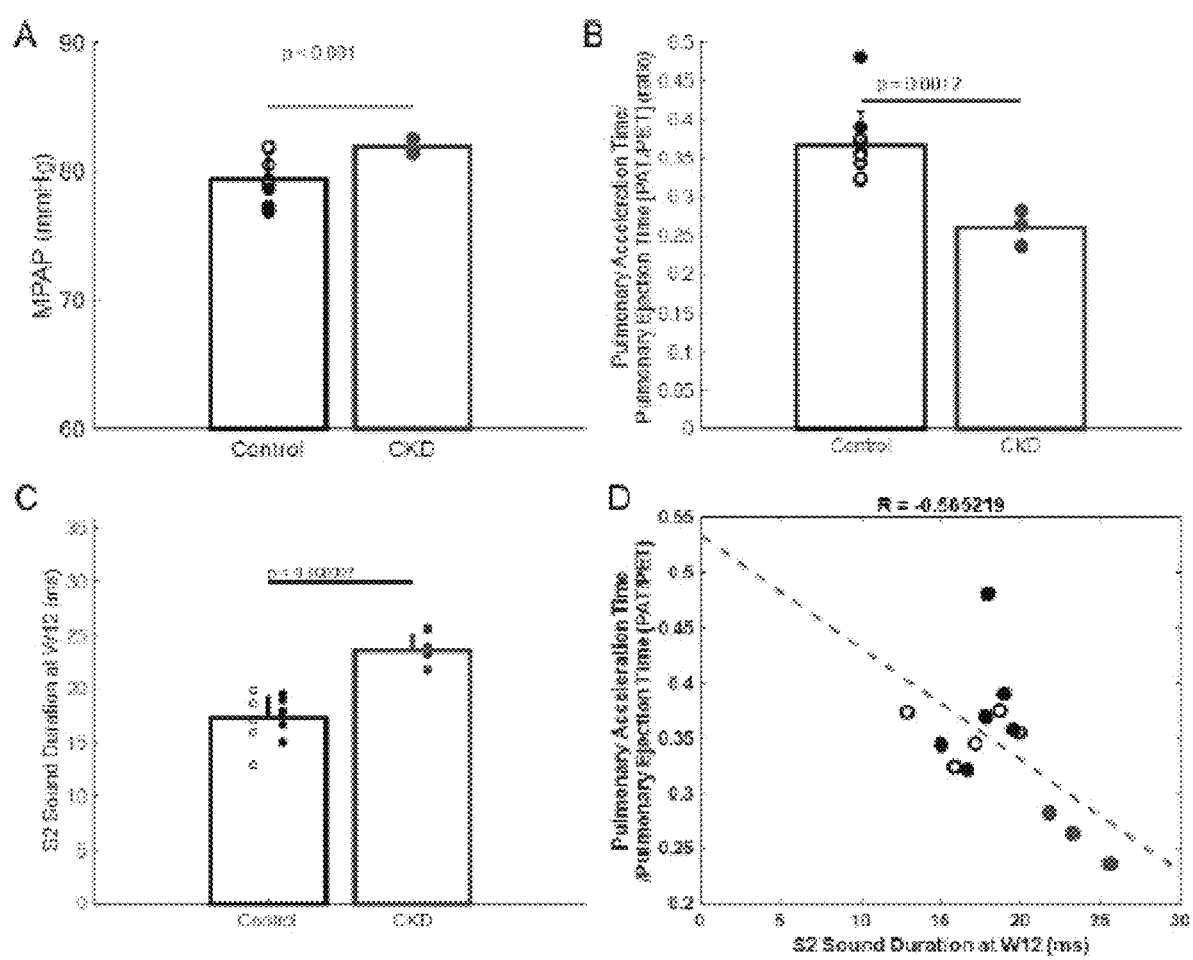
FIGS. 2A-2C show bar charts showing pulmonary pressure and S2 duration measures for HFpEF, each showing a control versus a CKD-induced model of HFpEF. In each plot, the control is the left bar, and the CKD-induced model is the right bar.
FIG. 2D shows a plot of PAT/PET versus S2 sound duration at W12 (in ms) for a control and a CKD-induced model of HFpEF. The three data points in the lower-right corner (at ~22 ms, ~23 ms, and ~26 ms) are for the CKD-induced model while the remaining data points are for the control. R=−0.565219.
Figure 3C:
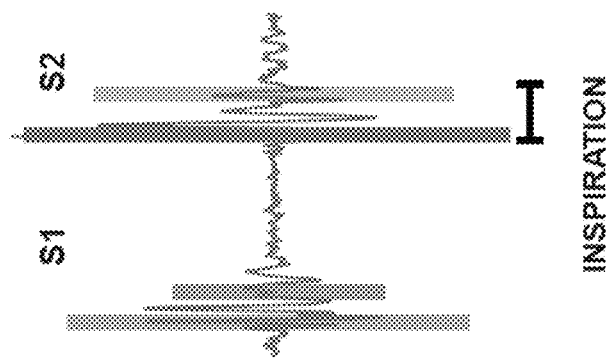
FIG. 3C shows a PCG of S1 and S2 during inspiration.
Figure 3B:
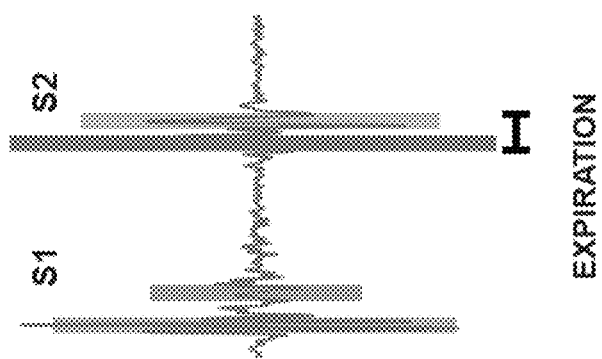
FIG. 3B shows a phonocardiogram (PCG) of S1 and S2 during expiration.
Figure 3A:
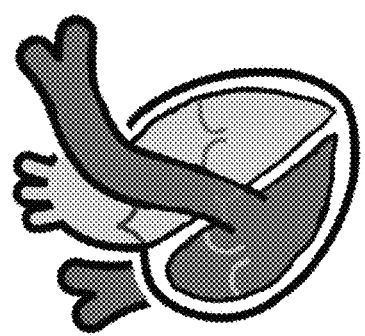
FIG. 3A shows a depiction of a heart, with brief descriptions of the first heart sound (S1) and the second heart sound (S2).

A method can be used to record and segment S2 sounds in anesthetized mice. Prior to echocardiographic assessment at the time points discussed above, a digital stethoscope can be used to record heart sounds in the mice for 60 seconds. Immediately following echocardiographic imaging, the mouse heart can be exposed, and a French fiber optic catheter can be used to record pulmonary artery pressure for 60 seconds. As expected in HFpEF, the preliminary data demonstrated increased mean pulmonary artery pressure in the CKD mice (FIG. 2A), which corresponds to echo measured reductions in pulmonary artery blood ejection (FIG. 2B). In support of the hypothesis that increased serum levels of CTnI and NT-proBNP are due to subtle alterations in heart remodeling that precede detectable changes in cardiac function, the S2 duration was significantly increased in the mice receiving the 12-week CKD diet regimen compared to chow fed controls (FIG. 2C). Plotting measures of pulmonary blood flow versus S2 duration demonstrated the correlation between these parameters, especially in the CKD mice (FIG. 2D). In FIG. 2D, the three data points in the lower-right corner (at ~22 ms, ~23 ms, and ~26 ms) are for the CKD mice while the remaining data points are for the control (R=−0.565219).

While mice have obvious anatomical differences compared to humans, the two species have similar blood pressure, and it is expected that the pathophysiological changes that result in S2 sound elongation would be conserved. Given the ~10-fold slower human heart rate compared to that of mice, the signal processing required to identify and analyze S2 sounds is expected to be easier in human patients. S2 length can be used as a low-cost, non-invasive measure of pulmonary artery pressure in HFpEF.

In order to analyze biomarker and cardiac remodeling, immediately following the pressure measurements the mice can be euthanized, and blood can be collected for analysis of CTnI and NT-proBNP. It can be expected to obtain ~500 microliters (μL) of blood per mouse. The blood can be processed to obtain serum, and the blood can be aliquoted into two portions. One aliquot can be used to measure CTnI and NT-proBNP by an enzyme-linked immunoassay (ELISA) (e.g., a commercially available ELISA). The other aliquot can be reserved for assay systems being developed as part of Thrust 1.1 efforts. The heart of each mouse can also be collected and cryo-sectioned for histological analysis of cardiac and myocyte structure.

Example 2

Figure 4:
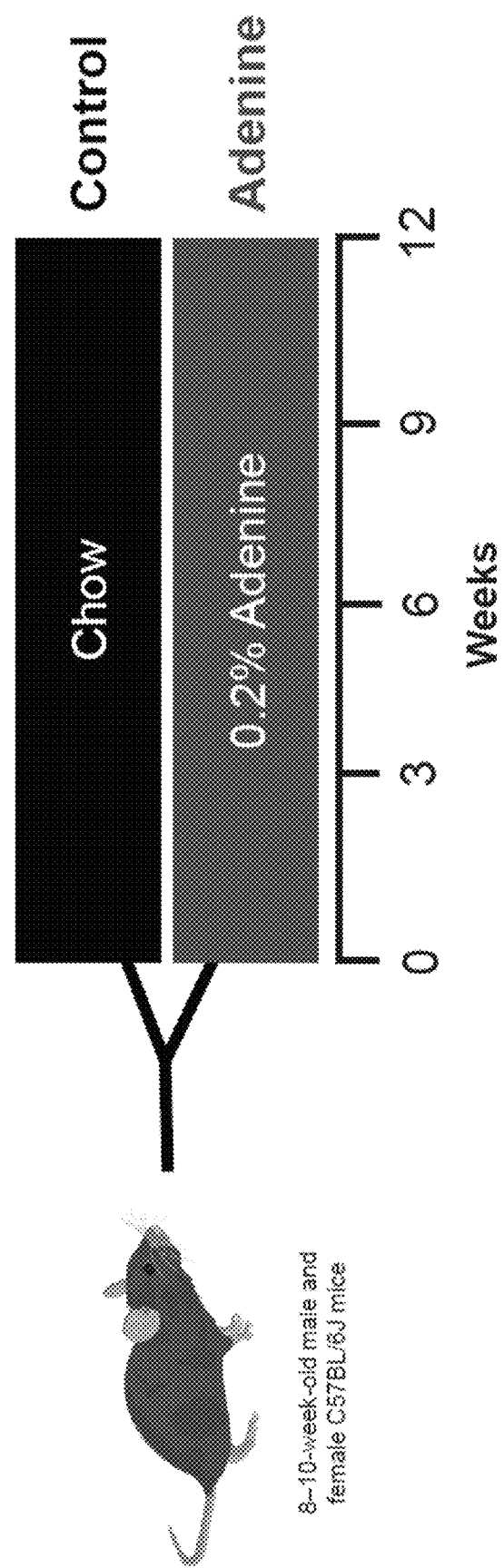
FIG. 4 shows a design view of a study where 8-10-week-old male and female C57BL/6J mice were given either a control (chow) or 0.2% adenine over a period of 12 weeks. The diet with adenine induces chronic kidney disease (CKD) and heart dysfunction in the mice. Measure markers of cardiac function included echocardiography, right-heart catheterization, and phonocardiography (ventilator, 60 breaths per minute).

CKD was induced in 8-10-week-old C57BL/6J male and female mice by supplementing chow pellets with 0.2% adenine for 12 weeks. A control group received no adenine. The study design is represented in FIG. 4. Measure markers of cardiac function included echocardiography, right-heart catheterization, and phonocardiography (ventilator, 60 breaths per minute).

Figure 5:
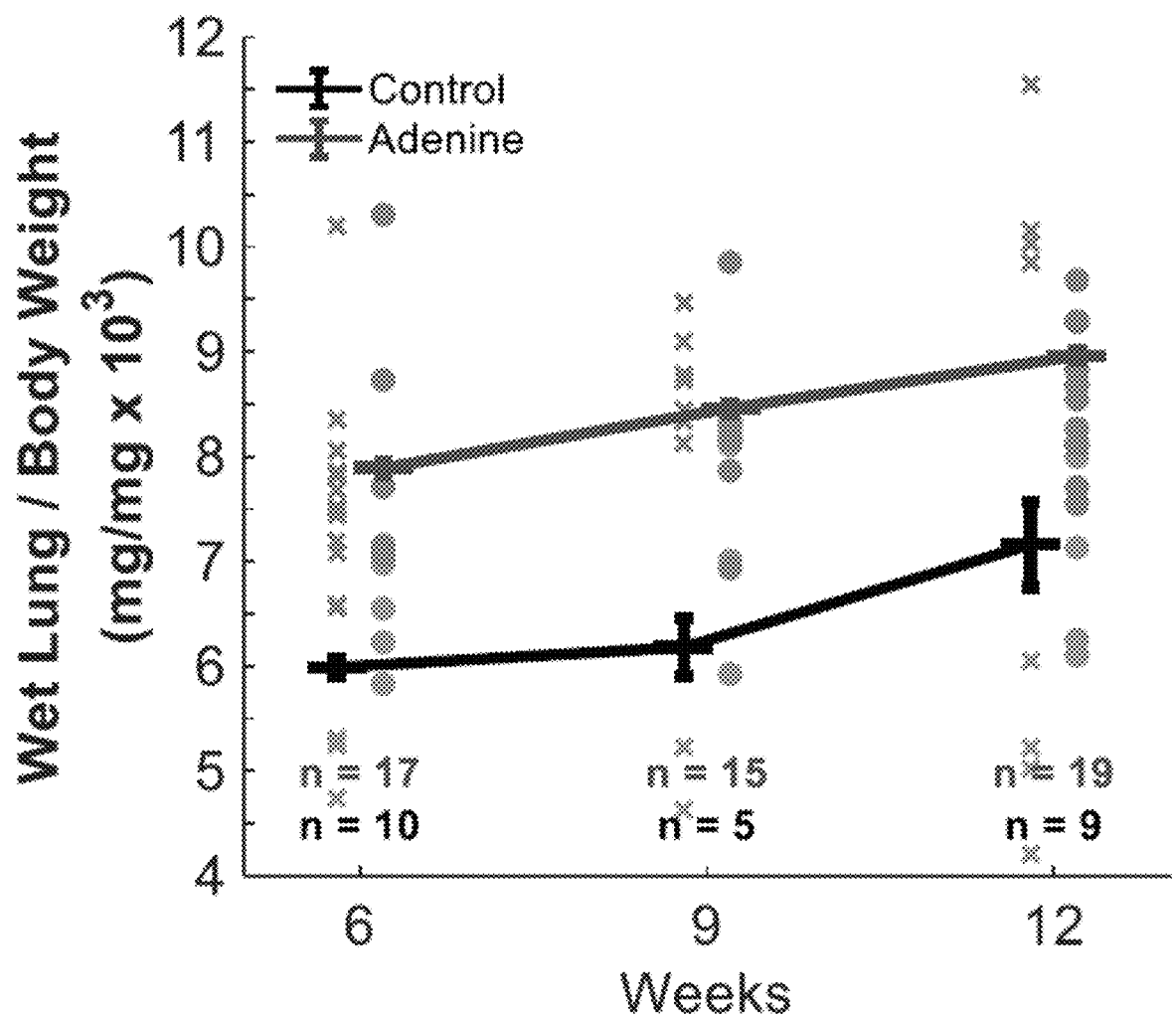
FIG. 5 shows a plot of wet lung/body weight (WL/BW) ratio (in milligrams per grams (mg/mg×$10^3$)) versus week number. An increase in WL/BW ratio is indicative of pulmonary edema, a marker of worsening heart failure. The n values that are shown lower on the graph (e.g., n=10 at 6 weeks) are for control, and the other n values are for adenine. The curve with the lower WL/BW ratios is for control, and the other curve is for adenine.
Figures 6A, 6B, 6C:
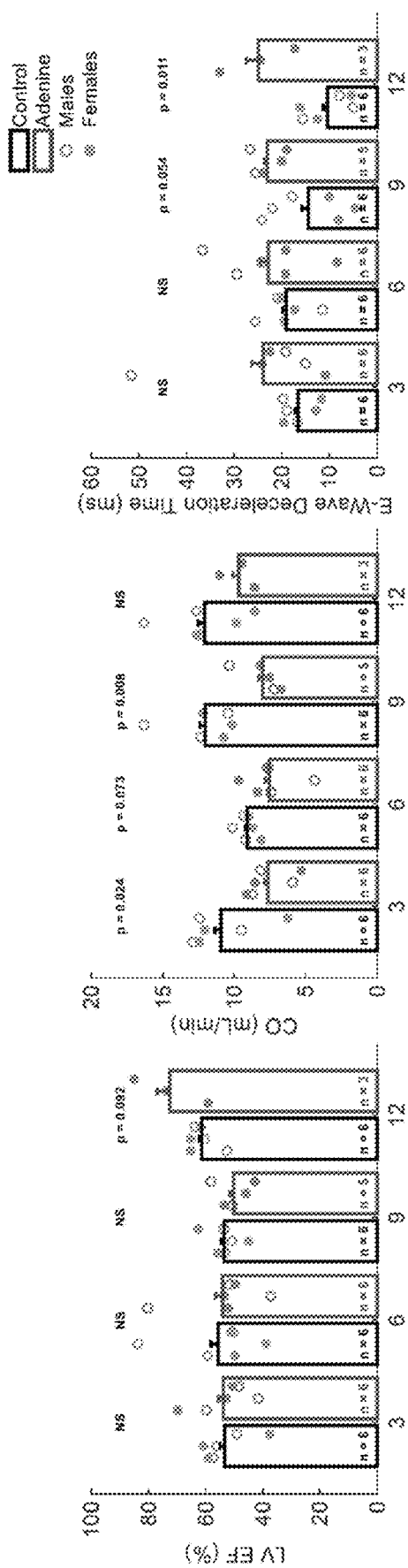
FIGS. 6A-6C show bar charts of left ventricle ejection fraction (LV EF) (in percentage (%)), cardiac output (CO) (in milliliters per minute (mL/min)), and e-wave deceleration time (in ms), respectively, each versus week number. In each bar chart, at each labeled week number, the left bar (and n value printed therein) is for control and the right bar (and n value printed therein) is for adenine. The data points are filled in if the mouse was female and a circle if the mouse was a male.

FIG. 5 shows a plot of wet lung/body weight (WL/BW) ratio versus week number. An increase in WL/BW ratio is indicative of pulmonary edema, a marker of worsening heart failure. FIGS. 6A-6C show bar charts of left ventricle ejection fraction (LV EF)), cardiac output (CO), and e-wave deceleration time, respectively, each versus week number. Adenine groups showed markers of heart failure with preserved ejection fraction. Prolonged deceleration time due to prolonged relation implies grade I diastolic dysfunction.

Figures 7A, 7B, 7C:
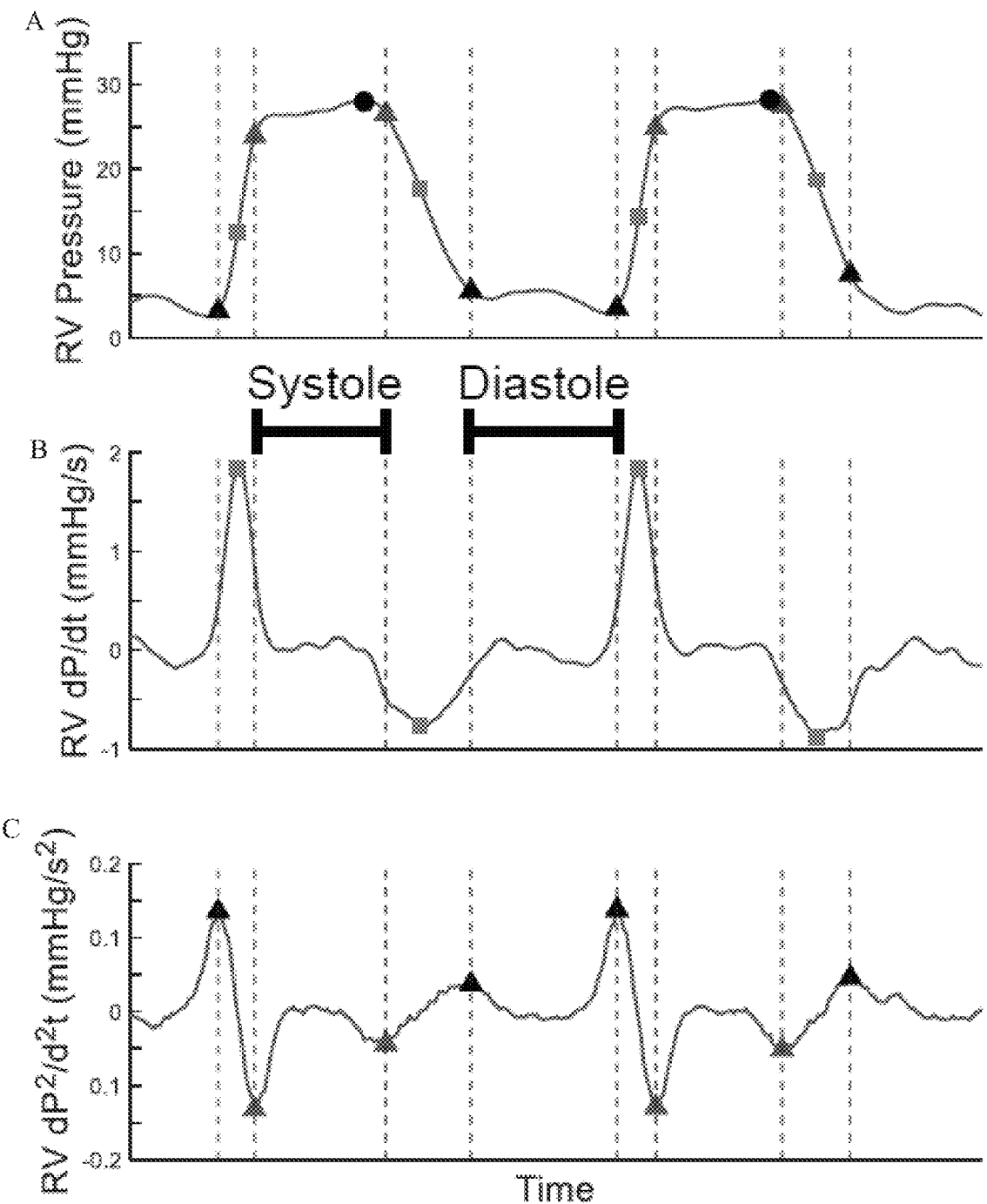
FIGS. 7A-7C show right ventricle (RV) pressure (in mmHg), change in RV pressure (dP/dt) (in mmHg per s (mmHg/s)), and the change in the change in RV pressure ($dP^2/d^2t$) (in mmHg per second squared ($mmHg/s^2$)), respectively, each versus time. The systole and diastole are marked with dotted vertical lines in FIG. 7B.

FIGS. 7A-7C show RV pressure, the first derivative (with respect to time) thereof, and the second derivative (with respect to time) thereof, respectively, each versus time. The systole and diastole are marked with dotted vertical lines in FIG. 7B.

Figure 8:
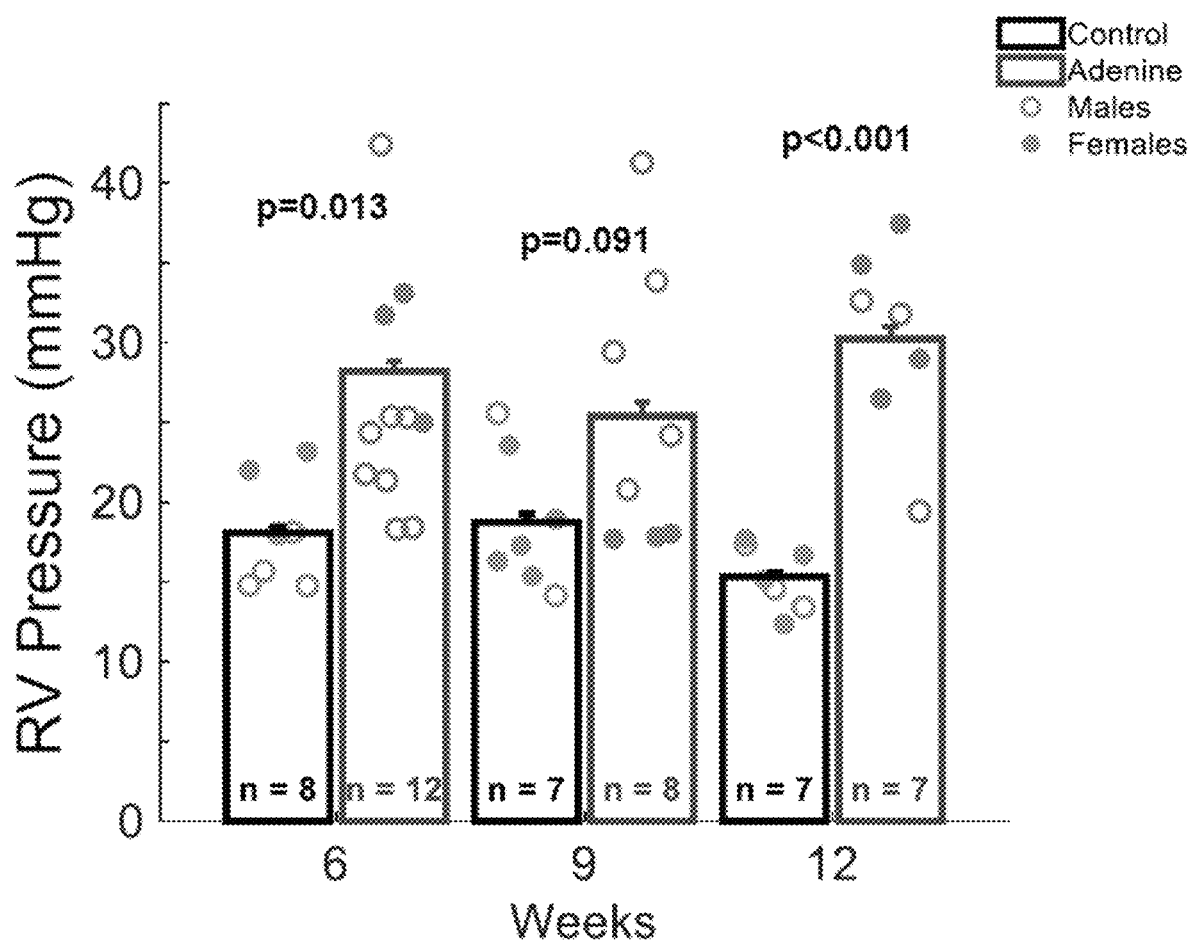
FIG. 8 shows a bar chart of RV pressure (in mmHg) versus week number. At each labeled week number, the left bar (and n value printed therein) is for control and the right bar (and n value printed therein) is for adenine. The data points are filled in if the mouse was female and a circle if the mouse was a male. The p values at 6 weeks, 9 weeks, and 12 weeks were 0.013, 0.091, and less than 0.001, respectively.

FIG. 8 shows a bar chart of RV pressure versus week number. Right-heart catheterization showed increased RV pressure, suggestive of RV dysfunction.

Figure 9:
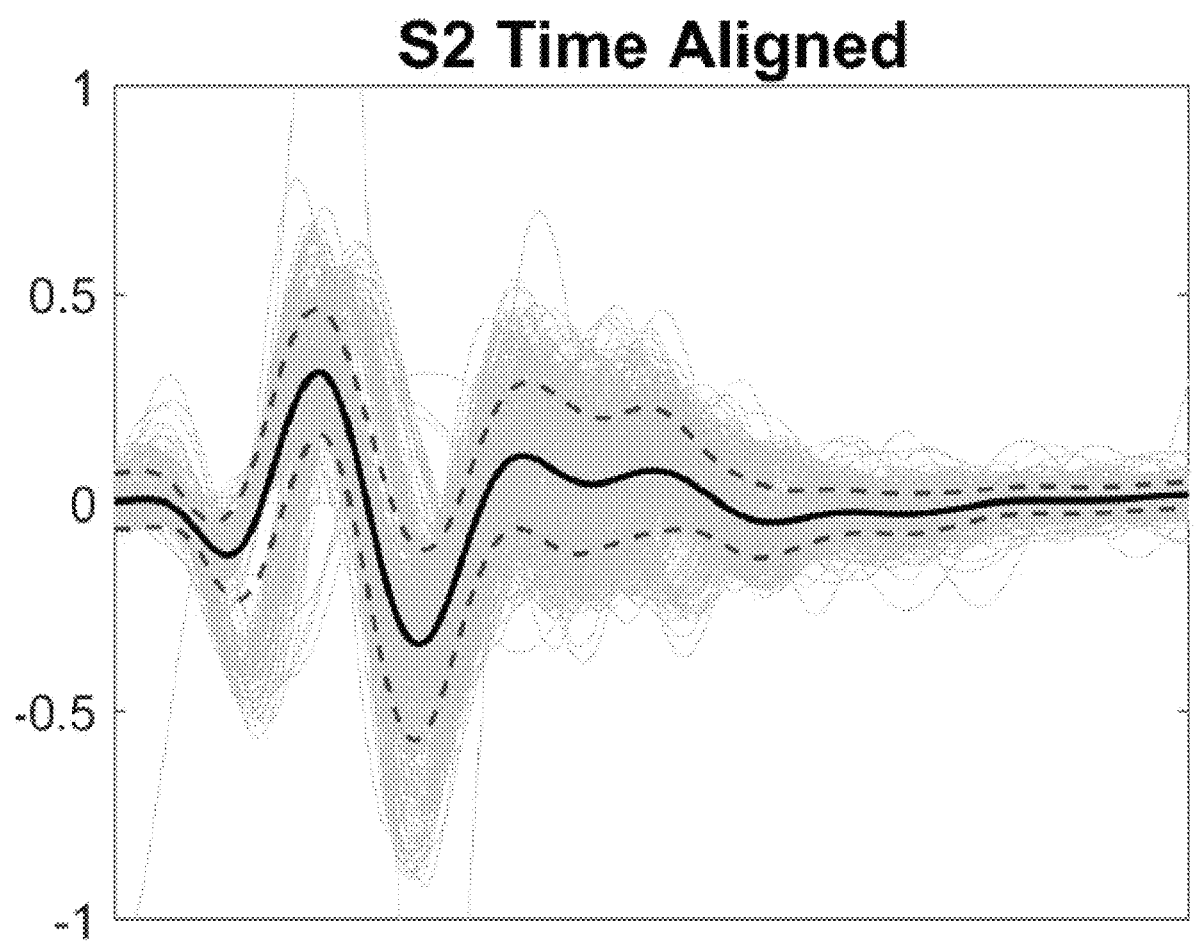
FIG. 9 shows an S2 time-aligned plot.
Figure 10:
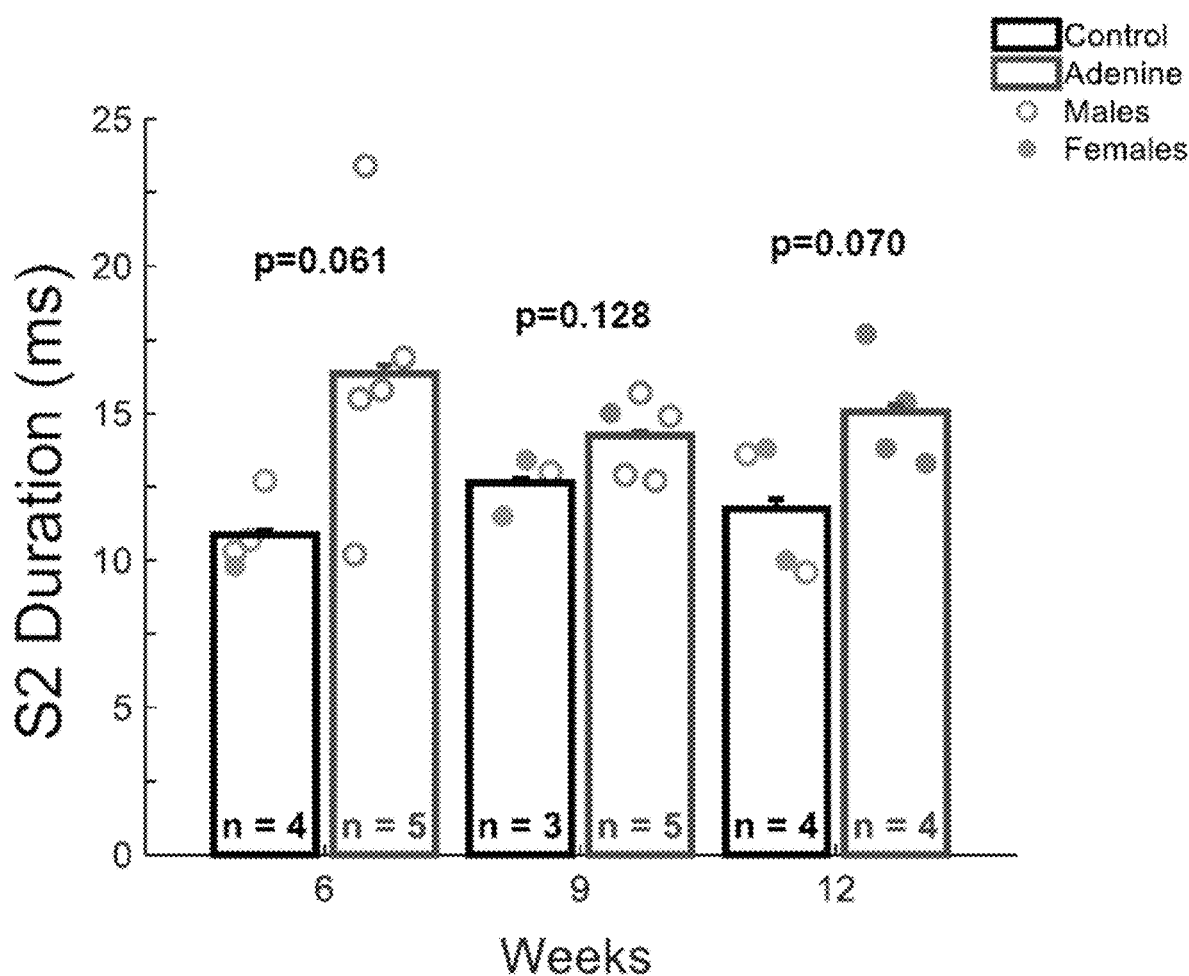
FIG. 10 shows a bar chart of S2 duration (in ms) versus week number. At each labeled week number, the left bar (and n value printed therein) is for control and the right bar (and n value printed therein) is for adenine. The data points are filled in if the mouse was female and a circle if the mouse was a male. The p values at 6 weeks, 9 weeks, and 12 weeks were 0.061. 0.128, and 0.070, respectively.

FIG. 9 shows an S2 time-aligned plot, and FIG. 10 shows a bar chart of S2 duration versus week number. S2 duration increased in the adenine group, including a delay in P2 closure.

Figure 11:
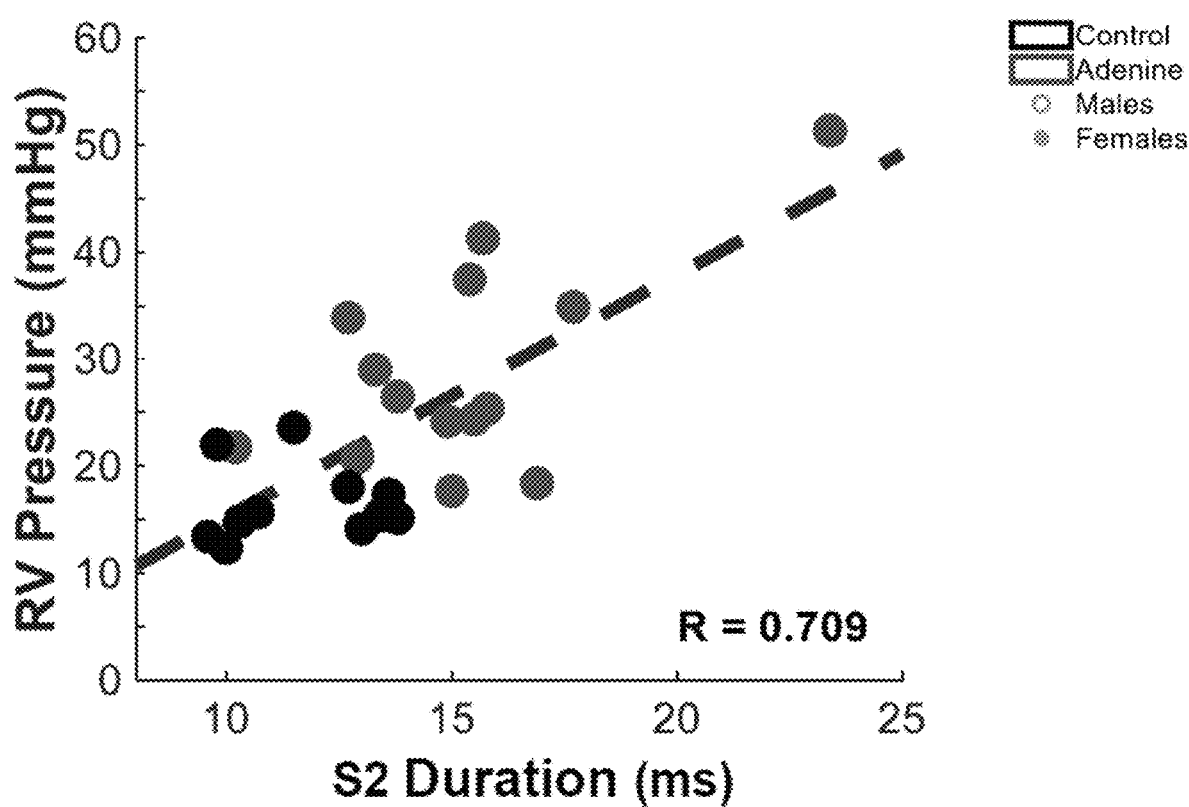
FIG. 11 shows a plot of RV pressure (in mmHg) versus S2 duration (in ms) for control and adenine groups. The data points clustered with the shorter S2 duration are for control, and the data points clustered with the higher S2 duration times are for adenine. The R value is 0.709.

FIG. 11 shows a plot of RV pressure versus S2 duration for the control and adenine groups. Referring to FIG. 11, a positive correlation between S2 duration and RV pressure (R=0.709) was observed, confirming that S2 duration can be used as a non-invasive tool to monitor heart failure.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including in the "References" section, if any) are incorporated by reference in their entirety, including all figures and tables, to the extent they are not inconsistent with the explicit teachings of this specification.

What is claimed is:

1. A system for identifying at least one marker of heart failure by quantifying a duration of an S1 heart sound and a duration of an S2 heart sound, the system comprising:
   a phonocardiograph;
   a processor in operable communication with the phonocardiograph; and
   a machine-readable medium in operable communication with the processor and having instructions stored thereon that, when executed by the processor, perform the following steps:
   using the phonocardiograph to record a phonocardiogram signal including, information of activity of a heart of a first patient;
   identifying at least one cardiac cycle including the S1 heart sound and the S2 heart sound;
   normalizing the at least one cardiac cycle;
   calculating a short-time Fourier transform of the signal;
   calculating an envelope of the signal using the short-time Fourier transform and the normalized at least one cardiac cycle;
   determining features of the signal based on the envelope of the signal, the features of the signal comprising the duration of the S1 heart sound and the duration of the S2 heart sound;
   correlating the features of the signal to measures of heart failure to identify the at least one marker of heart failure, the at least one marker of heart failure comprising any measure of heart failure with a strong correlation to the features of the signal; and using the at least one marker of heart failure to noninvasively monitor for heart failure of a second patient by checking a duration of an S2 sound of the second patient, the measures of heart failure comprising a timing of valve closure, a split time quantified by starts of sound components including M1 and T1, and a duration of heart sounds, and the measures of heart failure being measures that have been classified by echocardiography and cardiac catheterization.

2. The system according to claim 1, the signal being a phonocardiogram signal.

3. The system according to claim 1, further comprising a display in operable communication with the processor and the machine-readable medium, the instructions when executed further performing the step of displaying the at least one marker of heart failure on the display.

4. The system according to claim 1, the features of the signal further comprising a split time of the S1 heart sound, a split time of the S2 heart sound, a loudness of the S1 heart sound, and a loudness of the S2 heart sound.

5. The system according to claim 1, the measures of heart failure comprising pulmonary pressure, right ventricular pressure, and ejection fraction.

6. The system according to claim 1, the determining of the features of the signal based on the envelope of the signal comprising:

obtaining an envelope curve using a Hilbert transform on the envelope signal; and obtaining a start and an end of the envelope signal for each cycle.

7. The system according to claim 1, the correlating of the features of the signal to the measures of heart failure comprising using an algorithm.

8. The system according to claim 1, the calculating of the envelope of the signal comprising using at least one of a filtering technique and an averaging technique.

9. A method for identifying at least one marker of heart failure by quantifying a duration of an S1 heart sound and a duration of an S2 heart sound, the method comprising:

using, a phonocardiograph to record a phonocardiogram signal including information of activity of a heart of a first patient;

identifying at least one cardiac cycle including the S1 heart sound and the S2 heart sound;

normalizing the at least one cardiac cycle;

calculating a short-time Fourier transform of the signal;

calculating an envelope of the signal using the short-time Fourier transform and the normalized at least one cardiac cycle;

determining features of the signal based on the envelope of the signal, the features of the signal comprising the duration of the S1 heart sound and the duration of the S2 heart sound; and correlating the features of the signal to measures of heart failure to identify the at least one marker of heart failure, the at least one marker of heart failure comprising any measure of heart failure with a strong correlation to the features of the signal; and using the at least one marker of heart failure to noninvasively monitor for heart failure of a second patient by checking a duration of an S2 sound of the second patient, the measures of heart failure comprising a timing of valve closure, a split time quantified by start of sound components including M1 and T1, and a duration of heart sounds, and the measures of heart failure being measures that have been classified by echocardiography and cardiac catheterization.

10. The method according to claim 9, the signal being a phonocardiogram signal.

11. The method according to claim 9, further comprising displaying the at least one marker of heart failure on a display.

12. The method according to claim 9, the features of the signal further comprising a split time of the S1 heart sound, a split time of the S2 heart sound, a loudness of the S1 heart sound, and a loudness of the S2 heart sound.

13. The method according to claim 9, the measures of heart failure comprising pulmonary pressure, right ventricular pressure, and ejection fraction.

14. The method according to claim 9, the determining of the features of the signal based on the envelope of the signal comprising:

obtaining an envelope curve using a Hilbert transform on the envelope signal; and obtaining a start and an end of the envelope signal for each cycle.

15. The method according to claim 9, the correlating of the features of the signal to the measures of heart failure comprising using an algorithm.

16. The method according to claim 9, the calculating of the envelope of the signal comprising using at least one of a filtering technique and an averaging technique.

* * * * *